United States Patent [19]
Allen et al.

[11] 3,942,534
[45] Mar. 9, 1976

[54] DEVICE FOR TERMINATING TACHYCARDIA

[76] Inventors: Kenneth Roy Allen, 48 Wren Road; John Kenny, 4 Hobb's Way, both of Welwyn Garden City, Hertfordshire; Roworth Adrian John Spurrell, Flat 24, Delphian Port, Leigham Port Road, Streatham, London, all of England

[22] Filed: Nov. 21, 1974

[21] Appl. No.: 525,984

[30] Foreign Application Priority Data
Nov. 21, 1973 United Kingdom............... 54110/73

[52] U.S. Cl. ......................................... 128/419 PG
[51] Int. Cl.[2] .......................................... A61N 1/36
[58] Field of Search.......... 128/419 P, 419 PG, 421, 128/422, 423

[56] References Cited
UNITED STATES PATENTS

| | | | |
|---|---|---|---|
| 3,460,542 | 8/1969 | Gemmer....................... | 128/419 PG |
| 3,693,627 | 9/1972 | Berkovits...................... | 128/419 PG |
| 3,794,045 | 2/1974 | Thaler........................... | 128/419 PG |
| 3,845,773 | 11/1974 | Fontaine et al................ | 128/419 PG |

OTHER PUBLICATIONS
Cobbold et al., "Medical and Biological Engineering," Vol. 3, No. 10, 1965, pp. 273–278.
Merx et al., "Medical and Biological Engineering," Vol. 10, No. 2, Mar. 1972, pp. 297–300.

*Primary Examiner*—William E. Kamm
*Attorney, Agent, or Firm*—Wenderoth, Lind & Ponack

[57] ABSTRACT

A device for terminating tachycardia has an input part responsive to heartbeat signals. A tachycardia rate detector is connected to the input part and is effective to give an output while heartbeat signals occur at a rate characteristic of tachycardia. A gate circuit is connected to be controlled by the output from the tachycardia rate detector and a variable delay pulse circuit is connected to receive as input pulses heartbeat signals from the input part and give output pulses each a predetermined delay after a respective input pulse, the output pulses being applied as input to the gate circuit. An output circuit connected to supply stimulating pulses to the heart, the stimulating pulses being generated in response to gated pulses received from the gate circuit. A blocking circuit is connected to the gate circuit to ensure that output pulses from the gate are inhibited during a pause period following each output pulse. A feedback connection to the variable delay pulse circuit applies thereto feedback signals which alter the predetermined delay from one output pulse to the next.

12 Claims, 5 Drawing Figures

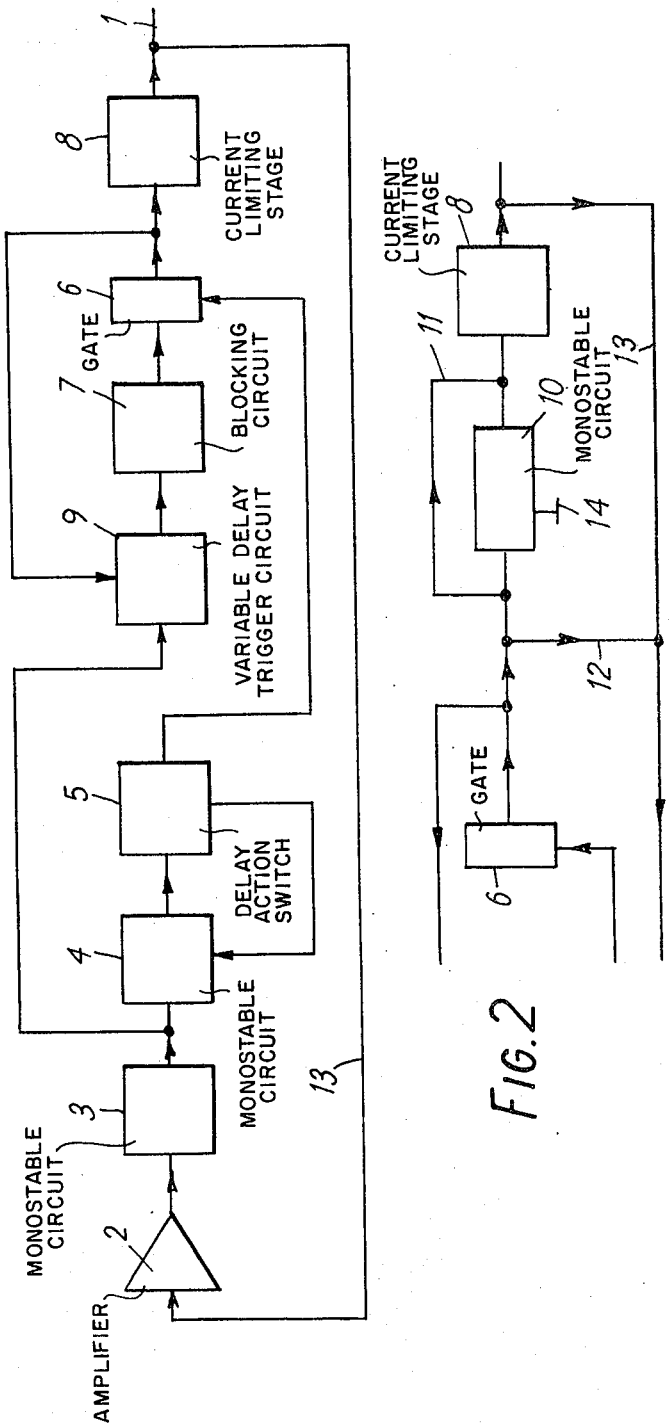

DEVICE FOR TERMINATING TACHYCARDIA

The invention relates to a device for terminating tachycardia. Tachycardia is a disturbance of the action of the heart resulting in severe increase of the rate of heartbeat. The invention is concerned particularly with the provision of an electrical device, which may or may not be of a kind implantable within the body, for terminating tachycardia.

According to the invention there is provided a device for terminating tachycardia comprising input means responsive to heartbeat signals; a tachycardia rate detector connected to the input means and effective to give an output while heartbeat signals occur at a rate characteristic of tachycardia; a gate circuit connected to be controlled by the output from the tachycardia rate detector; a variable delay pulse circuit connected to receive as input pulses heartbeat signals from the input means and give output pulses each a predetermined delay after a respective input pulse, the output pulses being applied as input to the gate circuit; an output circuit connected to supply stimulating pulses to the heart, the stimulating pulses being generated in response to gated pulses received from the gate circuit; a blocking circuit connected to the gate circuit to ensure that output pulses from the gate are inhibited during a pause period following each output pulse; and a feedback connection to the variable delay pulse circuit for applying thereto feedback signals which alter the said predetermined delay from one output pulse to the next.

It is found that tachycardia can be terminated by the application of an electrical stimulating pulse but successful termination depends on critical timing of the stimulating pulse in the heartbeat cycle. It is possible to terminate tachycardia by the generation of stimulating pulses at a constant rate on detection of tachycardia because sooner or later one of the stimulating pulses will occur at the appropriate time in a tachycardia cycle. However, by changing the delay time progressively the device of the present invention ensures that the correct timing is achieved in a more sure and positive manner.

Typically, the delay time between the P wave of the tachycardia heartbeat and the corresponding stimulating pulse or pulse group is changed from 150ms in steps of 5 or 10ms at each stimulating pulse or pulse group. While it is preferred that the delay of the variable delay pulse circuit should be altered progressively in increments it is clearly possible for the delay to be altered progressively in decrements from a maximum to a minimum. Alternatively, it may be arranged that the delays may be alternatively long and short, the long delays becoming progressively shorter and the short delays progressively longer.

The tachycardia rate detector preferably comprises a monostable circuit having an inherent pulse output time set to be slightly greater than the period between tachycardia pulses. Typically, for example the period between tachycardia P waves about 300ms. Therefore, under these circumstances the pulse length from the monostable circuit would be about 400ms. The rate detector further comprises a delayed-action switch which, in response to repeated triggering of the monostable circuit for a predetermined time switches the pulse output length of the monostable circuit to a long value — conveniently double. Response of the delayed-action switch also opens the above-mentioned gate circuit, thereby allowing stimulating pulses to pass to the heart.

Preferably the device has at its input a selective amplifier which is responsive to the frequency spectrum of typical P waves only and a monostable circuit which shapes the output from the selective amplifier to give pulses of predetermined length.

A feature of the invention is that the tachycardia device may be combined in a single unit with a bradycardia control device. Bradycardia is a condition where the heartbeat rate shows to an unacceptable level. Thus, for patients with bradycardia symptoms, or intermittent cardiac arrest a bradycardia control is provided in the form of a cardiac pacer which is inhibited unless the heart rate falls below a predetermined level, when stimulating pulses are issued. Such a pacer is called a demand pacer. Different types of demand pacer are described, for example, in British Pat. Nos. 1,333,552 and 1,335,530. In the tachycardia control device in accordance with the invention the input means and the output means may be used in conjunction with a bradycardia pacing rhythm circuit to constitute a demand pacer having an automatic tachycardia control facility. Thus, there may be provided a tachycardia control device as described in combination with a bradycardia control circuit, the bradycardia control circuit comprising a pacing rhythm circuit connected to receive heartbeat signals from the input means and having an output connected to the output circuit, the bradycardia control circuit being effective to give an output pulse to the output circuit and thereby generate a stimulating pulse if no heartbeat signal is received within a certain delay time after an immediately preceding heartbeat signal or stimulating pulse. The said certain time delay may be fixed or it may be variable as described in British Pat. No. 1,335,530, for example.

The invention will further be described with reference to the accompanying drawing, of which:

FIG. 1 is a block diagram of a device in accordance with the invention;

FIG. 2 is a drawing illustrating a modification of the FIG. 1 device;

Figure 3:
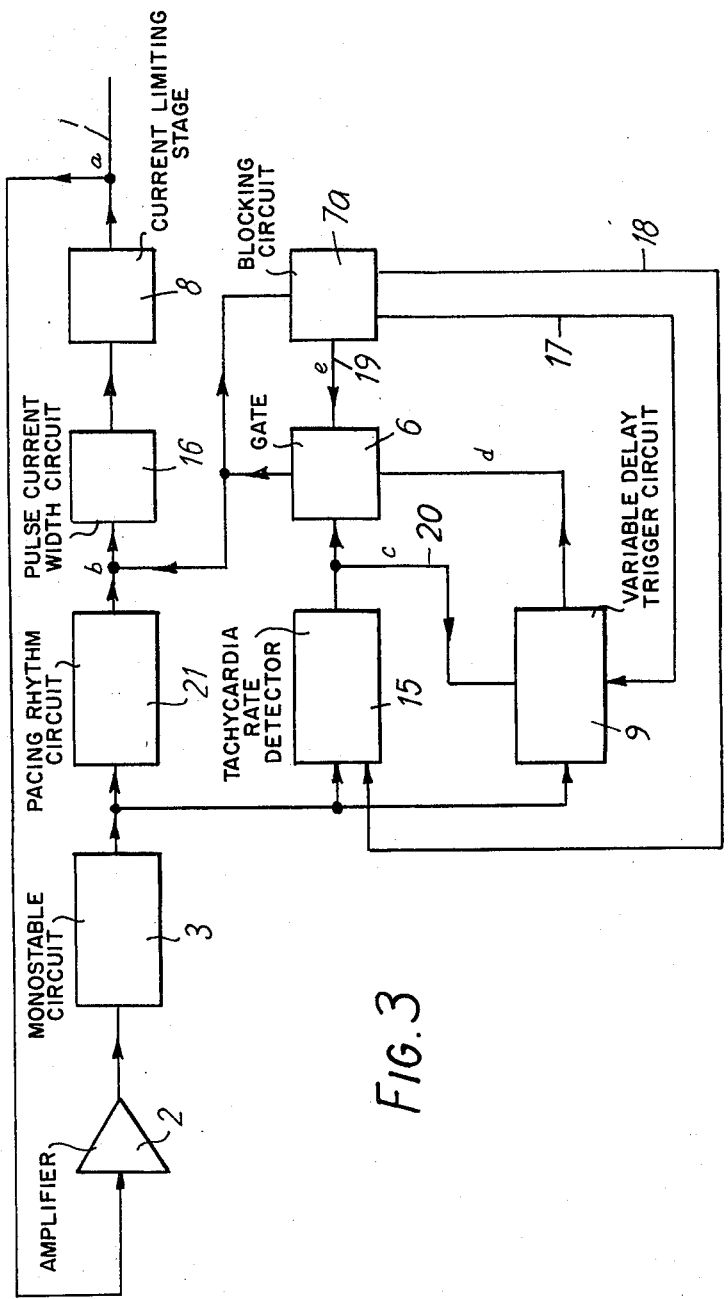
FIG. 3 is a block diagram of a device in accordance with the invention in combination with a bradycardia control circuit.

Referring to FIG. 1 the device comprises a terminal 1 to which is connected in use a catheter (not shown) which carries an electrode to be positioned in the heart. Pulses are applied via this electrode to stimulate the heart. The electrode is also used as a sensing electrode and electrocardiac signals representative of the heart activity are picked up by the electrode and passed to a selective amplifier 2 at the input of the circuit. The selective amplifier 2 is a three-stage combined active filter and amplifier and is designed to reject frequencies outside the energy spectrum of atrial P waves. On detection of a P wave signal the amplifier 2 triggers a monostable circuit 3. Circuit 3 is a complementary transistor monostable circuit which triggers immediately a P wave is sensed by the amplifier 2 and which delivers an output pulse a predetermined length in the range 100–150ms. The circuit is not affected during the pulse period by further incoming pulses.

Output pulses from circuit 3 trigger a second monostable circuit 4 which is another complementary transistor circuit which triggers immediately when the circuit 3 triggers. Circuit 4 delivers output pulses of a preset length. The length is preset in accordance with the periodic frequency of tachycardia pulses of the particular patient being treated. Typically, such tachycardia signals are below a repetitive frequency of 400ms and accordingly circuit 4 may typically be set to give a pulse length of 400ms. If circuit 4 receives further input signals during the time an output pulse is being delivered it will retrigger.

The output from circuit 4 is applied to a delayed-action switch 5 which responds only if a signal is received which is longer than 1 second duration. In practice this condition means that about three tachycardia P wave signals have been detected. In responding, the delayed-action switch 5 operates to open a gate 6 and also feeds back a signal to the circuit 4 in order to alter the pulse length output of that circuit to 800ms. The combination of circuit 4 and switch 5 is a tachycardia rate detector which gives an output when tachycardia is detected, the output persisting until tachycardia ceases.

Gate 6, when open, allows pulses to pass from a blocking circuit 7. Such pulses are stimulating pulses which pass through a current-limiting stage 8 to the terminal 1. Circuit 7 is triggered by the output from a variable-delay trigger circuit 9, which circuit produces a trigger pulse a certain time after the start of each output pulse from circuit 3. Initially, the delay time of the circuit 9 is 150ms. Thus, in the presence of tachycardia a stimulating pulse is applied to the terminal 1 at a time 150ms after a P wave is detected. However, there is a feedback path from the output of gate 6 to the circuit 9 and this applies feedback signals, each of which increases the delay time of circuit 9 by 10ms. Thus, the next time circuit 9 responds to a signal the triggering output will be given after a delay of 160ms.

Blocking circuit 7 includes a monostable arrangement which has a delay of 800ms so that after each stimulating pulse the circuit is blocked for 800ms and immediately succeeding P waves will have no effect. If the tachycardia condition persists after the 800ms pause period then another stimulating pulse will be generated, this being after a delay of 160ms following a respective P wave. It will be seen, therefore, that the delay time for successive stimulating pulses progressively increases by 10ms at a time and there is a pause period of 800ms after each stimulating pulse during which period another stimulating pulse cannot be issued. Circuit 9 is such that when the delay time has progressively risen from 150ms to 250ms the next feedback signal from the output of gate 6 causes the delay time to revert immediately to 150ms whereafter the cycle is repeated until tachycardia ceases.

Output stimulating pulses fed back directly from terminal 1 to amplifier 2 will not result in further stimulating pulses because at this time the circuit will be blocked by virtue of the action of the blocking monostable circuit in circuit 7.

Because of the progressive increase of the delay time a stimulating pulse, if not originally generated at the appropriate time in the tachycardia cycle, will, within a short time, achieve the critical timing. Tachycardia will then be inhibited. Under these conditions the interval between the stimulus and the following P wave exceeds the period of monostable circuit 4 which is now 800ms. Circuit 4 will then switch off and the delayed action switch will immediately switch off, thus closing the gate 6. Stimulation will stop and the normal sinus rhythm is restored.

Under normal sinus conditions, when the heart is beating naturally, the circuit will not operate to give stimulating pulses because although monostable circuit 4 will be triggered at each P wave, the succeeding P wave will occur after 400ms and the circuit 4 will have switched off. Therefore, the delayed-action switch 5 will not sense the circuit 4 having been switched on for a period of 1 second. The gate 6 will remain closed.

When tachycardia is terminated and the stimulating pulses cease the delay of circuit 9 will gradually sink back to the starting value of 150ms. The rate of decrease is typically 5ms per second at a delay time of, say, 200ms. Thus if the tachycardia should stop and restart after several seconds the delay would only have drifted back by a small amount and will still be close to the critical value which will stop the tachycardia. Therefore, termination of the tachycardia will take a short time only.

As far as interference is concerned, under steady interference conditions (e.g., 50Hz. pick-up) provided the period of the waveform is less than the blocking period of circuit 3 (100–150ms) then the circuit 3 will be repeatedly retriggered and will remain on. No output pulses will be given from circuit 3 and no stimulating pulses will be generated. This will happen for interference frequencies of pulses per minute or above.

Transient interference can only cause the device to give a premature stimulus, under normal sinus rhythm conditions, if it reoccurs within the period of circuit 4 and outside the period of circuit 3, i.e., 150 to 400ms. It must also reoccur over a period of at least 600ms so that the delayed action switch 5 will switch on.

Under tachycardia conditions transient interference can cause the variable delay trigger circuit 9 to restart but a stimulation can only occur if a transient falls outside the blocking time of monostable circuit 7.

Referring now to FIG. 2 there is shown a modification which may be made to the embodiment of FIG. 1 to give an additional preferred feature. The modification consists in interposing a variable delay monostable circuit 10 between the gate 6 and the current-limiting output stage 8 of the FIG. 1 device. The monostable circuit 10 is by-passed by a lead 11 and an additional connection 12 is made to the feedback path 13 from the circuit output to the input of amplifier 2. The effect of the monostable circuit 10 is to add to each output pulse a second pulse which occurs a predetermined time later. Thus, stimulating pulses are issued in groups of two. The delay between the two pulses is adjusted to suit a particular patient by a manual control 14 of circuit 10. A feedback signal is given for each output pulse.

Referring now to FIG. 3 there is shown another embodiment of the invention. In FIG. 3 the device comprises a catheter electrode 1 connected to a selective amplifier 2 which drives a blocking circuit 3 as in the FIG. 1 embodiment. The output from circuit 3 is applied to a tachycardia rate detector 15 which is the same as the combination 4 and 5 of FIG. 1. Gate 6 is provided to be controlled by the output from the rate detector 15 to pass pulse signals from a variable delay pulse circuit 9 to an output circuit. The variable delay pulse circuit 9 receives input pulses from circuit 3 in the same way as in FIG. 1. Thus far, the operation of the device of FIG. 3 is precisely the same as that of the device of FIG. 1. The gated output pulses from gate 6 are applied to an output circuit comprising a pulse width circuit 16 which generates a pulse of 1ms. duration on being triggered and a current limiting ouput stage 8. The pulses applied from stage 8 to electrode 1 are cardiac stimulating pulses.

In the device of FIG. 3 the blocking circuit 7 of FIG. 1 is replaced by a blocking circuit 7a. Circuit 7a has a pause period of approximately 1.5 seconds instead of 800ms of the FIG. 1 embodiment. Input pulses to circuit 7a are derived from the output of gate 6. In response to each input pulse the circuit 7a produces a blocking output on lines 17 and 18 lasting for the pause period. The output on line 17 is applied to gate 6 to hold the gate closed for the pause period and that on line 18 is applied to hold the rate detector circuit 15 in the "on" state for the duration of the pause period. Circuit 7a also provides the feedback pulses over a line 19 to change the delay of circuit 9 incrementally at each pulse after the manner of the FIG. 1 embodiment. There is an additional connection 20 from the output of detector 15 to the circuit 9 which provides an enabling signal to enable the cricuit 9 to function while tachycardia is being detected.

It will be seen that the circuit described thus far operates in a very similar manner to that of FIG. 1 and the overall function is substantially the same. The principal difference of the FIG. 3 embodiment is in the provision of a pacing rhythm circuit 21 for the treatment of bradycardia. Circuit 21 receives input pulses from circuit 3 and triggers circuit 16 to give stimulating pulses if the input pulse rate is below a threshold level of about 60 pulses per minute, the heart rate being, say, 70 pulses per minute. The threshold level can be adjusted to suit individual patients.

Circuit 21 operates by initiating a delay period corresponding to one pulse period at the threshold rate on receipt of a pulse. If the delay period expires before the receipt of the next pulse a stimulating pulse is issued. If the next pulse is received before the expiry of the delay period the delay cycle is restarted and no stimulating pulse is issued. If natural sinus rhythm stops altogether successive input pulses to circuit 21 will be derived over the feedback path 13 from stimulating pulses and there will be a continuous train of pulses issued at the threshold rate. When natural sinus rhythm restarts at a rate above the threshold rate then stimulating pulses are inhibited. The pacing rhythm circuit may be of the kind shown in British Pat. No. 1,338,382 for example.

Figure 4:
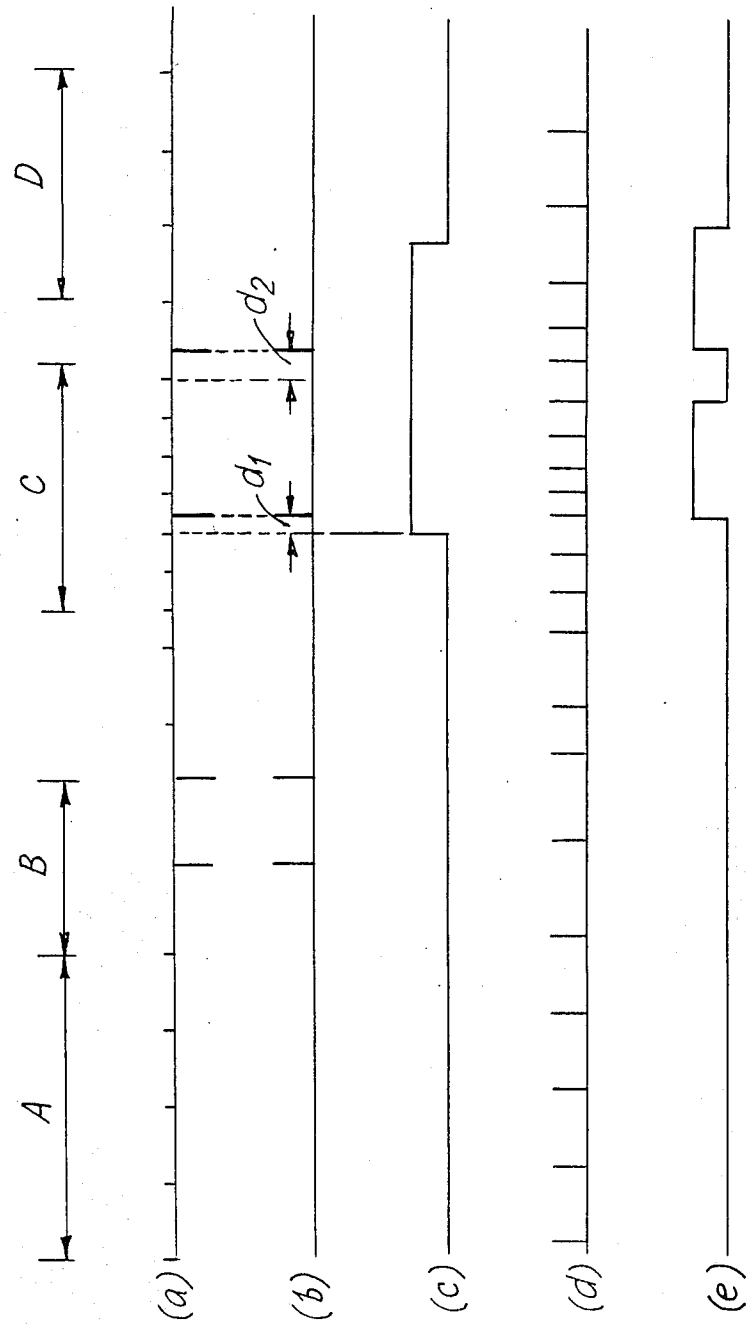
FIG. 4 is a waveform diagram for illustrating the operation of the circuit of FIG. 3.

FIG. 4 shows typical waveforms of the circuit of FIG. 3 at points (a) to (e) respectively. There is illustrated a sequence of cardiac conditions as follows: firstly, during period A the heart beats naturally at a rate of 70 pulses per minute; during period B bradycardia occurs and circuit 21 issues two stimulating pulses; normal heart function is restored and then at period C tachycardia occurs; two stimulating pulses are issued by the tachycardia control circuit and then normal sinus rhythm is restored at period D.

In waveform (a) the P waves are shown as small positive spikes and the stimulating pulses large negative spikes.

In waveform (d) the pulses are delayed by 150ms. from each detected pulse of waveform (a), whether natural or stimulated, until a further incremental delay is introduced on the second output pulse from gate 6. Thus, delay $d_1$ of waveform (b) is 150ms whereas delay $d_2$ is 155ms, the increment in this case being 5 ms per pulse.

Waveform (c) shows the time during which tachycardia is detected by circuit 15 and waveform (e) shows the blocking pulses during the pause periods generated by circuit 7a.

Figure 5:
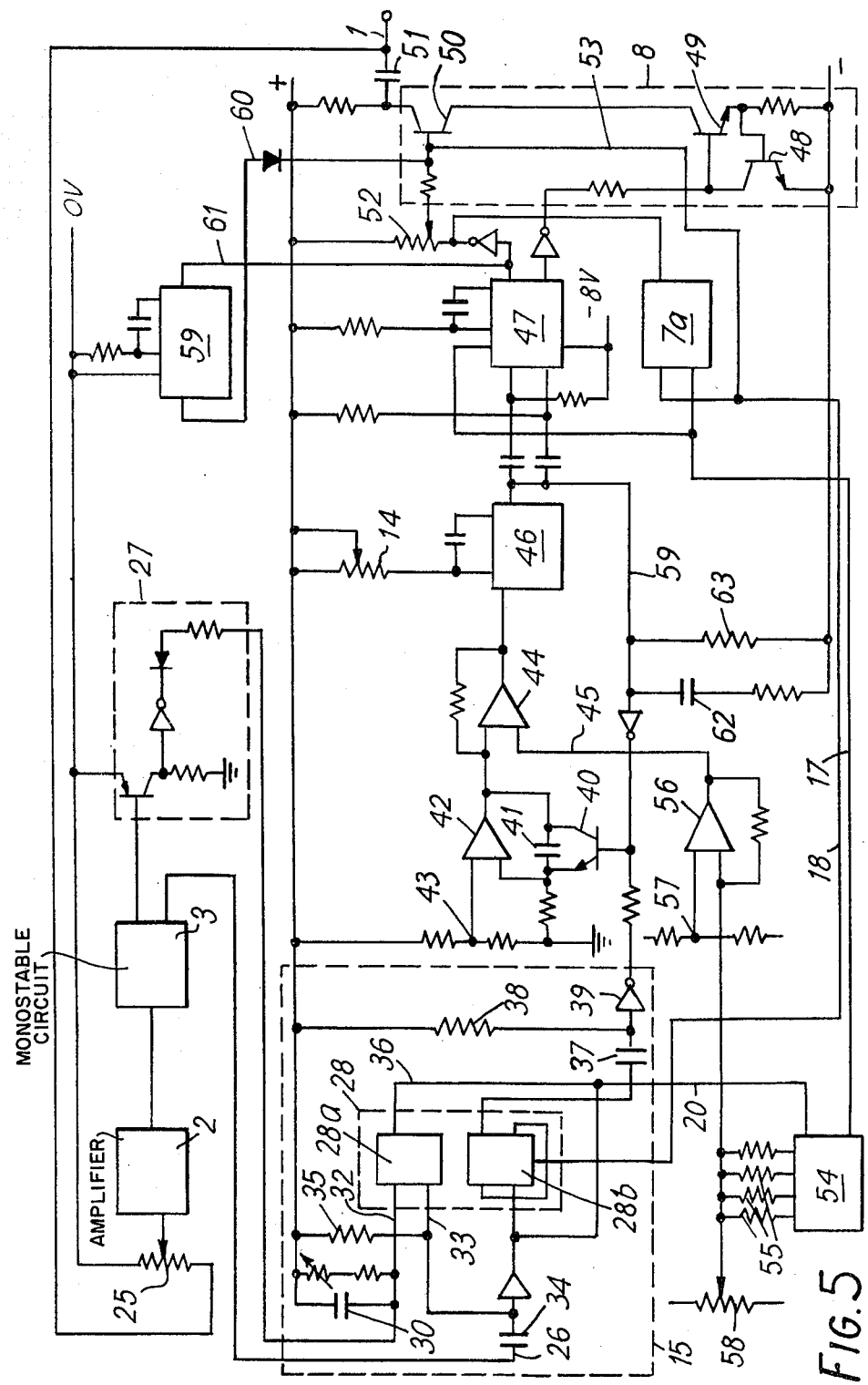
FIG. 5 is a detailed circuit diagram of a device in accordance with the invention.

Referring now to FIG. 5 there is shown a detailed circuit diagram of a device for terminating tachycardia having the features of the tachycardia portion of the FIG. 3 device together with the double-pulse feature of the FIG. 2 device. The same reference numerals will be used where appropriate.

In FIG. 5 the catheter electrode 1 is connected to the input of selective amplifier 2 via a variable resistor 25 which acts as a sensitivity control. Amplifier 2 is an integrated circuit of type 3821–MS. The output from amplifier 2 is applied to a blocking circuit 3 which is an integrated circuit of type 3821 and which gives a first output to tachycardia rate detector 15 over a line 26 and a second output to a pulse-shaper circuit 27. Rate detector 15 comprises an integrated circuit 28 of type CD 4013 which is shown in two halves 28a and 28b. For each input pulse to amplifier 2 the output from pulse-shaper 27 is a 10msec pulse which follows shortly after the pulse on line 26. The 10msec pulses are applied over a line 29 to an RC circuit comprising a capacitor 30 and a variable resistor 31. Capacitor 30 charges rapidly and discharges slowly at a rate determined by resistor 31 and the ouput from the RC circuit, which is a ramp waveform for each pulse, is applied to an input 32 of half-circuit 28a. Half-circuit 28a has a clock input 33 which receives the pulses from line 26 after differentiation by capacitor 34 and resistor 35. An output pulse is given from output 36 of half-circuit 28a if, at the time of the clock pulse, the level of the signal on input 32 is above a predetermined threshold level. If not, no output pulse is given. Thus, when a clock pulse arrives at input 33 it will give rise to an output pulse from output 36 if it follows so soon after the preceding pulse that the preceding ramp waveform has not decayed below the threshold level. Thus this is a pulse rate detector and the tachycardia pulse rate at which detection is achieved is set by resistor 31.

Half-circuit 28b is connected as a divide-by-two counter and receives the output pulses from output 36. The purpose of this is to ensure that the first tachycardia pulse does not give rise to a detection signal but only the second pulse. The chance of faulty and spurious operation is thereby lessened.

The output from half-circuit 28b is applied through a differentiating circuit comprising a capacitor 37 and a resistor 38 and through an invertor 39 to the base of a transistor 40. transistor 40 is connected across the feedback capacitor 41 of a Miller integrator including an operational amplifier 42. The other input to the amplifier 42 is derived from a reference source 43 and when transistor 40 is switched off by the output from rate detector 15 a ramp waveform is initiated. The ramp waveform is applied to a Schmitt trigger circuit 44 which receives a reference voltage on a line 45 and which triggers to deliver an output pulse when the ramp voltage exceeds the reference voltage. Thus, an output pulse is given from circuit 44 after a certain delay following a tachycardia pulse, which delay depends upon the level of the reference applied on line 45.

The output from circuit 44 is applied to a monostable circuit 46 which is half of an integrated circuit type MC14528CP, the other half being shown at 47. Circuit 46 gives a pulse output of length 150 to 300ms depending on the setting of a variable resistor 14. The leading edge of the output pulse triggers one input of circuit 47 and the trailing edge triggers another input of circuit 47. Consequently, two output pulses are given from circuit 47 for each pulse from circuit 46, which pulses are spaced apart a time corresponding to the setting of control 14. The output pulses from circuit 47 trigger an output circuit 8 which comprises three transistors 48, 49 and 50. The output from transistor 50 constitutes the cardiac stimulating pulses applied, through a capacitor 51, to the catheter 1.

An adjustable control 52 is provided to set the level of the stimulating pulses. Control 52 is connected to the output from blocking circuit 7a and the arrangement is such that if the blocking circuit gives an output transistor 50 is blocked thereby and no stimulating pulses can be given. The input to blocking circuit is derived from the base of transistor 50 by a connection 53 so that after each stimulating pulse the circuit is blocked against issuing further pulses for 1.5 seconds. A blocking output is applied over a line 19 to block 47 for the blocking, or pause, period and signals derived from connection 53 are applied over line 18 to circuit 28b to cancel the divide-by-two function so that the tachycardia detection output is effectively held while stimulating pulses are being issued and a detection signal is achieved for each tachycardia pulse.

As was mentioned above, the delay generated by circuits 42 and 44 between the tachycardia pulse and the corresponding stimulating pulse is determined by the level of the signal on line 45. This signal level is set by a four-bit binary counter 54 which receives clock input pulses from a line 17 connected to the pause output of blocking circuit 7a. Each time a stimulating pulse is issued, a clock pulse is received by counter 54. Counter 54 has an enabling input connection 20 connected to output 36 so that clock pulses are counted only if a tachycardia detection signal is present. The digital parallel output from counter 54 is weighted by binary graded resistors 55 and scanned to give an analogue input to a differential amplifier 56 which receives a reference input 57. The output of amplifier 56 is applied to line 45.

The counter 54 counts input pulses cyclically up to a maximum of 15 and then resets to zero to resume the cycle. Each unit of the count represents a delay increment of 10msec. The zero level delay is set at 150 msec or so and may be adjusted by a control 58.

Two further blocking controls are provided to prevent over-rapid stimulation in the event of failure of other components. The first of these back-up controls is an integrated circuit 59 type MC14528CP which receives input pulses derived from the base of transistor 50 by a connection 60 and which subsequently holds off further stimulating pulses by application of a blocking output on line 61 for a period of 150msec. This ensures that the spacing between the double stimulating pulses cannot be less than 150msec which might be dangerous.

The second back-up blocking control comprises the combination of a capacitor 62 and a resistor 63, which combination receives output pulses from circuit 46 and produces a blocking voltage at the base of transistor 40, the blocking voltage decaying by discharge of capacitor 62 through resistor 63 and lasting as a blocking level for half a second. Thus, in the event of failure of blocking circuit 7a, stimulating pulse pairs cannot be closer than half a second apart.

The invention is not restricted to the details of the embodiments described above with reference to the accompanying drawing. For example, the increment by which the delayed changes at each step may be more or less than 10ms perhaps being 5ms. for instance. In an alternative arrangement the variable-delay circuit may be controlled directly from the delayed-action switch — a steady potential being applied by the switch 5 while it is on so as to give a continuously progressive change in delay time for the circuit 9.

Instead of sensing atrail waves, as described, the circuit may respond to ventricular R waves, stimulation being applied to a ventricle.

The internal feedback connection 13 may be disconnected and two separate catheters used instead, one at the input for sensing the P or R waves and the other at the output for stimulating an atrium or ventricle as appropriate.

We claim:

1. A device for terminating tachycardia comprising input means responsive to heartbeat signals; a tachycardia rate detector connected to the input means and effective to give an output while heartbeat signals occur at a rate characteristic of tachycardia; a gate circuit connected to be controlled by the output from the tachycardia rate detector; a variable delay pulse circuit connected to receive as input pulses heartbeat signals from the input means and give output pulses each a predetermined delay after a respective input pulse, the output pulses being applied as input to the gate circuit; an output circuit connected to supply stimulating pulses to the heart, the stimulating pulses being generated in response to gated pulses received from the gate circuit; a blocking circuit connected to the gate circuit to ensure that output pulses from the gate are inhibited during a pause period following each output pulse; and a feedback connection to the variable delay pulse circuit for applying thereto feedback signals which alter the said predetermined delay from one output pulse to the next.

2. A device as claimed in claim 1 wherein the variable delay circuit responds to the pulses from the feedback connection to alter the delay progressively in increments from a minimum limit to a maximum limit.

3. A device as claimed in claim 1 wherein the output circuit includes a pulse generator connected to generate a plurality of spaced stimulating pulses in response to each output pulse from the gate circuit.

4. A device as claimed in claim 3 wherein the pulse generator has an adjustable control whereby the spacing of the spaced stimulating pulses may be adjusted.

5. A device as claimed in claim 1 wherein the blocking circuit is connected to receive an input from the output of the gate circuit and to apply a control signal to close the gate circuit for the pause time thereafter.

6. A device as claimed in claim 5 wherein the blocking circuit has a second output wherefrom feedback signals are applied by the feedback connection to the variable delay circuit and a third output connection to the tachycardia rate detector whereby the tachycardia rate detector is held in a condition corresponding to detected tachycardia for the pause time.

7. A device as claimed in claim 1 wherein the blocking circuit is connected to receive the output pulses from the variable delay circuit and apply them to the gate circuit, the blocking circuit effecting a blocking function and applying no further pulses to the gate circuit during the pause time after each pulse applied to the gate circuit.

8. A device as claimed in claim 1 wherein a second blocking circuit is provided in the input means, the second blocking circuit being responsive to each heartbeat signal to provide a pulse for application to the tachycardia rate detector and the variable delay pulse circuit, which pulse is of a length equal to a predetermined blocking period.

9. A device as claimed in claim 1 wherein the tachycardia rate detector comprises a monostable circuit which, in response to each input pulse, gives an output pulse of a length slightly longer than the period between tachycardia heartbeats, and a delayed action switch connected to the output of the monostable circuit to respond only if the monostable circuit output has persisted for more than a predetermined time.

10. A device as claimed in claim 9 wherein there is a feedback connection from the delayed action switch to the monostable circuit whereby the pulse period of the monostable circuit is lengthened when the delayed action switch responds.

11. A device as claimed in claim 1 in combination with a bradycardia control circuit, the bradycardia control circuit comprising a pacing rhythm circuit connected to receive heartbeat signals from the input means and having an output connected to the output circuit, the bradycardia control circuit being effective to give an output pulse to the output circuit and thereby generate a stimulating pulse if no heartbeat signal is received within a certain delay time after an immediately preceding heartbeat signal or stimulating pulse.

12. A device for terminating tachycardia comprising input means responsive to heartbeat signals; a tachycardia rate detector connected to the input means and effective to give an output while heartbeat signals occur at a rate characteristic of tachycardia; a pulse generator circuit connected to be controlled by the output from the tachycardia rate detector to give output pulses each a predetermined delay after a corresponding heartbeat signal; a variable delay circuit connected to control the said predetermined delay; an output circuit connected to supply stimulating pulses to the heart, the stimulating pulses being generated in response to output pulses received from the pulse generator circuit; a blocking circuit connected to the pulse generator circuit to ensure that output pulses from the pulse generator circuit are inhibited during a pause period following each stimulating pulse; and a feedback connection to the variable delay pulse circuit for applying thereto feedback signals which alter the said predetermined delay from one output pulse to the next.

* * * * *